United States Patent [19]
Leclerc et al.

[11] Patent Number: 6,051,679
[45] Date of Patent: Apr. 18, 2000

[54] SELF-ACID-DOPED HIGHLY CONDUCTING POLYTHIOPHENES

[75] Inventors: Mario Leclerc; Martine Chayer; Karim Faïd, all of Québec, Canada

[73] Assignee: Universitéde Montréal, Montréal, Canada

[21] Appl. No.: 09/214,998

[22] PCT Filed: Jul. 3, 1997

[86] PCT No.: PCT/CA97/00477

§ 371 Date: Jan. 15, 1999

§ 102(e) Date: Jan. 15, 1999

[87] PCT Pub. No.: WO98/03499

PCT Pub. Date: Jan. 29, 1998

Related U.S. Application Data

[60] Provisional application No. 60/022,307, Jul. 22, 1996.

[51] Int. Cl.[7] .................. C08G 75/00; C07D 333/34; H01B 3/18; G21F 1/10
[52] U.S. Cl. .................. 528/380; 523/137; 524/910; 549/66; 252/500
[58] Field of Search .................. 528/380, 377; 523/137; 524/910; 549/66; 252/500

[56] References Cited

U.S. PATENT DOCUMENTS

| | | | |
|---|---|---|---|
| 4,987,042 | 1/1991 | Jonas et al. | 528/379 |
| 4,992,559 | 2/1991 | Kathirgamanathan et al. | 549/66 |
| 5,093,033 | 3/1992 | Feldhues et al. | 252/500 |
| 5,367,041 | 11/1994 | Wudl et al. | 528/392 |

FOREIGN PATENT DOCUMENTS

| | | |
|---|---|---|
| 0 253 594 | 1/1988 | European Pat. Off. . |
| 0 257 573 | 3/1988 | European Pat. Off. . |
| 6-192440 | 7/1994 | Japan . |
| 94 02530 | 2/1994 | WIPO . |

OTHER PUBLICATIONS

"A Facile Preparation of a Self–Doped Conducting Polymer", Y. Ikenoue et al. J. of the Chem. Soc., Chem. Commun. pp. 1694–1695, 1990.

"Functionalized Regioregular Polythiophenes: Towards the Development of Biochromic Sensors", Faid K. et al. Chem. Commun. (24), pp. 2761–2762, 1996.

*Primary Examiner*—Tae Yoon
*Attorney, Agent, or Firm*—Connolly Bove Lodge & Hutz LLP

[57] ABSTRACT

The invention relates to thiophenes bearing (ω-sulfonate) alkoxy or (ω-sulfonic acid)alkoxy groups and water-soluble polythiophenes bearing (ω-sulfonic acid)-alkoxy side-chains prepared therefrom. The invention also relates to methods for the preparation of these compounds and to antistatic coatings and EMI shieldings comprising the polythiophenes.

15 Claims, No Drawings

SELF-ACID-DOPED HIGHLY CONDUCTING POLYTHIOPHENES

This is a Continuation of a Provisional application Ser. No. 60/022,307 filed on Jul. 22, 1996.

The invention relates to thiophenes bearing (ω-sulfonate)alkoxy or (ω-sulfonic acid)alkoxy groups and water-soluble polythiophenes bearing (ω-sulfonic acid)alkoxy side-chains prepared therefrom. The invention also relates to methods for the preparation of these compounds and to antistatic coatings and EMI shieldings comprising the polythiophenes.

The search for processable, stable, conducting polymers has been the goal of many studies in the past few years. Many synthetic approaches have been taken but, generally, the conducting state is obtained through a partial chemical or electrochemical oxidation (so-called doping reaction) of the conjugated moieties leading to the formation of different mobile charge carriers (radical cations, dimerized radical cations and dications).

In most cases, processability has been obtained by the introduction of large counter-ions (which are introduced during the oxidation process to preserve the electro-neutrality) or by the attachment of relatively flexible side chains. It is believed that these structural modifications decrease the attractive interchain interactions and introduce favorable interactions between the substituents and the solvent.

The addition of side-chains does not only allow an easier processing of some electroactive polymers, but can also modulate the electronic properties of the conjugated main chain. For instance, it has been reported that the introduction of strong electrondonating side-chains, e.g. alkoxy groups, decreases the oxidation potential of the resulting polymers, giving a better stability of the oxidized (and conducting) state.

In U.S. Pat. No. 5,093,033 and Macromolecules 24(1991)455, poly(3-alkoxythiophene)s are disclosed, Macromolecules 26(1993)2501 teaches poly(3,3'-dialkoxy-2,2'-bithiophene)s and poly(4,4'-dialkoxy-2,2'-bithiophene)s. Poly(3,4-cylcloalkoxythiophene)s are known from U.S. Pat. No. 4,987,042. All these materials show high and stable electrical conductivities with low absorption in the visible range when oxidized.

On the other hand, it has been found that the presence of different counter-ions in the doped state can significantly alter the stability of the electrical conductivity. For instance, it is believed that steric interactions between the flexible side-chains and the counter-ions are responsible for the poor stability of some of these conducting polymers, particularly at high temperatures. A partial solution to this problem was the attachment of ionic (e.g. sulfonate moieties) side-chains which allows the possibility to get the counter-ions covalently linked to the conjugated backbone (combined to a good solubility in water), leading to the concept of self-doped conducting polymers. For instance, U.S. Pat. No. 5,367,041 discloses self-doped zwitterionic polythiophenes bearing alkylsulfonate or alkylcarboxylate side-chains.

It is worth noting that an external redox reaction must be done onto the conjugated polymer to obtain the oxidized (conducting) state but this process does not involve the introduction of any counter-ions during the doping process.

Macromolecules 26(1993)7108 and J. Chem. Soc. Chem. Commun. (1990)1694 disclose that the preparation of the acid form of sulfonated polythiophenes(involving a sulfonic acid fuctionality) is accompanied by a partial doping (oxidation) without the use of any external oxidizing agent. Thus, the presence of a strong protonic acid, oxygen (air), and a conjugated backbone can lead to conducting (doped) polymers.

Following a new synthetic approach, water-soluble polythiophenes bearing (ω-sulfonic acid)alkoxy side-chains have now been synthesized showing stable, high electrical conductivities together with low absorption in the visible range.

One aspect of the invention is to provide monomers from which such polymers can be prepared. These monomers are thiophenes corresponding to formula (I)

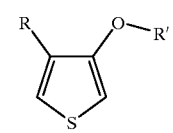

(I)

and bithiophenes corresponding to formulae (IIa) or (IIb)

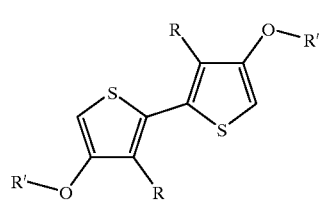

(IIa)

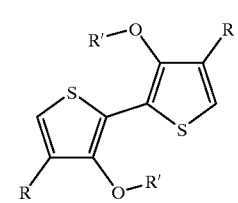

(IIb)

In these formulae R represents a hydrogen atom or a $C_1$–$C_4$ alkyl group. R is preferably hydrogen or methyl, ethyl, propyl, isopropyl, butyl, isobutyl or tert.-butyl. Still more preferably R represents hydrogen or methyl in the thiophenes of formula (I) and hydrogen in the bithiophenes of formula (II), respectively.

R' is —$(CH_2)_n$—$SO_3M$ with n=2 to 12, preferably n=2, and M=H, Li, Na, K, Rb, Cs, $NH_4$, preferably M=Na.

Another aspect of the invention is to provide a method for the preparation of these thiophenes and bithiophenes. They can be prepared by first reacting a 3-bromothiophene, a 4,4'dibromo-2,2'-bithiophene, or a 3,3'dibromo-2,2'-bithiophene, respectively, with $NaOCH_3$ in the presence of CuBr to form the methoxy-substituted compound, i.e. a 3-methoxythiophene, a 4,4'-dimethoxy-2,2'-bithiophene, or a 3,3'-dimethoxy-2,2'-bithiophene, respectively. This compound is then reacted with an ω-haloalkanol HO—$(CH_2)_n$—X (X=Cl, Br, I, preferably X=Br; n=2–12, preferably n=2), in the presence of $NaHSO_4$. The resulting product, a 3-(ω-haloalkoxy)thiophene, a 4,4'-di(ω-haloalkoxy)-2,2'-bithiophene), or a 3,3'-di(ω-haloalkoxy)-2,2'-bithiophene), respectively, is then reacted with $M_2SO_3$ (M=H, Li, Na, K, Rb, Cs, $NH_4$, preferably M=Na, K, $NH_4$) to form the desired thiophene or bithiophene, respectively.

The polymers of the invention comprise recurring units of formulae (III) or (IV)

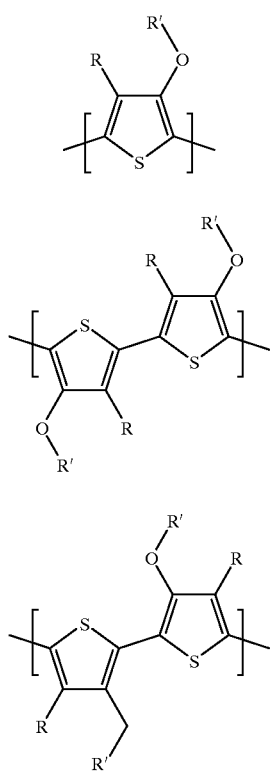

In these formulae R represents a hydrogen atom or a $C_1-C_4$ alkyl group. R is preferably hydrogen or methyl, ethyl, propyl, isopropyl, butyl, isobutyl or tert.-butyl. Still more preferably R represents hydrogen or methyl in the units of formula (III) and hydrogen in the units of formula (IV), respectively.

R' is —$(CH_2)_n$—$SO_3M$ with n=2 to 12, preferably n=2, and M=H, Li, Na, K, Rb, Cs, $NH_4$. In one preferred embodiment M is sodium, in another preferred embodiment, M is hydrogen.

The polymers of the invention can be conveniently prepared by polymerizing the thiophenes or bithiophenes in the presence of an oxidant. In most cases $FeCl_3$ is used for this purpose, but it is well known in the art that other oxidants can also be employed. The thiophenes or bithiophenes can also be polymerized electrochemically.

A convenient method for obtaining the polymers in the sulfonic acid form (M=H) is to first polymerize a monomer bearing alkali sulfonate or ammonium sulfonate groups and then dissolve the resulting polymer in water and pass the solution through an ion-exchange resin to produce the sulfonic acid form of these polymers.

Alternatively, the monomer bearing the alkali sulfonate or ammonium sulfonate groups can be passed through an ion-exchange resin to produce the sulfonic acid form which can be polymerized as described above.

The polymers of the invention can be used as starting materials for the production of anti-static coatings or EMI shieldings. It is therefore also an aspect of the invention to provide anti-static coatings or EMI shieldings comprising the polymers of the invention. Preferably, the anti-static coatings or EMI shieldings contain the sulfonic acid form of these polymers.

EXAMPLES

Example 1

3-methoxy-4-methylthiophene 22.3 g of 3-bromo-4-methylthiophene were added to a mixture of 80 mL sodium methoxide (25% in methanol), 30 mL of NMP and 11 g of CuBr. The mixture was refluxed for 3 days and after cooling, was filtrated and washed with water. The compound was extracted several times with diethyl ether. The organic phase was dried with magnesium sulfate and then evaporated. The resulting oil was purified by chromatography on a silica gel column with hexanes as eluent. Yield 98%.

$^1$H-NMR ($CDCl_3$, ppm): 6.75 (1H, d); 6.08 (1H, d); 3.72 (3H,s); 2.04 (3H, s)

$^{13}$C NMR ($CDCl_3$, ppm): 156.74; 128.53; 119.81; 95.35 56.79; 12.33

3-(2-bromo)ethoxy-4-methylthiophene 4.2 g of 3-methoxy-4-methylthiophene was added to a mixture of 40 mL of toluene, 8.2 g of 2-bromo-1-ethanol (Aldrich) and 500 mg of $NaHSO_4$. The resulting mixture was heated until the produced methanol had been distilled off and the temperature rose to 110° C. The product was cooled and washed several times with water and, subsequently, extracted with diethyl ether. The organic phase was dried with magnesium sulfate and then evaporated. The product was purified by column chromatography using silica gel and hexanes as eluent. Yield=55%.

$^1$H NMR: ($CDCl_3$, ppm): 6.83 (1H, d); 6.18 (1H, d); 4.25 (2H,t); 3.63 (2H, t); 2.11 (3H,s)

$^{13}$C NMR ($CDCl_3$, ppm): 155.06; 129.18; 120.33; 97.23; 69.65; 29.20; 12.71

Sodium 3-(2-sulfonate)ethoxy-4-methylthiophene 2.5 g of 3-(2-bromo)ethoxy-4-methylthiophene in 20 mL of acetone was added to a mixture of 1.5 g of $Na_2SO_3$ in 20 mL of water. The mixture was refluxed for 3 days. After cooling, the unreacted product was extracted with diethyl ether. The aqueous phase was then evaporated, giving a white crystalline powder. The desired product was recrystallized in a mixture of water/ethanol (1:1) at −10° C. Yield=60%. M.P.: 228° C.

$^1$H NMR ($D_2O$, ppm): 7.01 (1H, d); 6.51 (1H, d); 4.38 (2H, t); 3.39 (2H, t); 2.08 (3H, s)

$^{13}$C NMR ($D_2O$, ppm): 155.52; 130.13; 121.41; 98.92; 68.57; 50.91; 28.85; 11.83

Example 2

3-(2-bromo)ethoxythiophene 5.00 g of 3-methoxythiophene (Aldrich) was solubilized with 11.00 g of 2-bromoethanol in 20 mL of toluene, then 2.00 g of $NaHSO_4$ was added in one portion. The mixture was heated and methanol was distilled off. The solution was cooled and washed with water and diethylether. The organic phase was dried with magnesium sulfate. After evaporation, a brown liquid was obtained which was purified by column chromatography on silica gel using a mixture of $CCl_4$ and $CHCl_3$ (9:1) as the eluent. An oil was recovered which was further purified by recrystallization in methanol. White crystals were then obtained with a yield of 67%. M.P.=46° C.

$^1$H NMR (CDCl$_3$, ppm): 7.18 (1H, m); 6.78 (1H, m); 6.28 (1H, m); 4.27 (2H, t); 3.63 (2H, t)

$^{13}$C NMR (CDCl$_3$, ppm): 156.54; 124.79; 119.16; 98.12; 69.65; 28.62

Sodium 3-(2-sulfonate)ethoxythiophene

To a solution of 0.48 g of Na$_2$SO$_3$ in 5.00 mL of water was added a solution of 527 mg of 3-(2-bromo)ethoxythiophene dissolved in 10 mL of acetone. The mixture was allowed to reflux for 48 hrs. The solution was then cooled and washed with diethyl ether. The aqueous phase was separated and evaporated under reduced pressure. The crude product was dissolved in water and few drops of ethanol was then added to induce the precipitation of the inorganic salt. The suspension was filtered and evaporated.

A white crystalline product was obtained with a yield of 37%. This product decomposes at temperatures above 290° C. before melting.

$^1$H NMR (D$_2$O, ppm): 7.46 (1H, m); 6.96 (1H, m); 6.70 (1H, m); 4.50 (2H, t); 3.47 (2H, t)

$^{13}$C NMR(D$_2$O,ppm): 156.96; 126.50; 120.11; 100.25; 66.25; 50.92

Example 3

4,4'-Dimethoxy-2,2'-bithiophene 3.13 g of 4,4'-dibromo-2,2'-bithiophene was solubilized in 90 mL of sodium methoxide (25% in methanol) and 50 mL of NMP. 3.50 g of CuBr was then added in one portion and the solution was put to reflux for 24 hrs. The resulting suspension was washed with water and diethyl ether. The organic phase was separated and dried with magnesium sulfate.

After evaporation of the solvent, a greenish solid was obtained which was purified by chromatography on silica gel using a mixture of CCl$_4$ and CHCl$_3$ (9:1) as the eluent. A greenish solid was obtained with a yield of 37%. M.P.: 94° C.

$^1$H-NMR (CDCl$_3$, ppm): 6.81 (2H, d); 6.13 (2H, d); 3.79 (6H, s)

$^{13}$C NMR (CDCl$_3$, ppm): 158.17; 136.07; 115.56; 95.96; 57.13

4,4'-Di(2-bromo)ethoxy-2,2'-bithiophene

The product was prepared from a reaction between 529 mg of 2-bromoethanol, 1.00 g of NaHSO$_4$ and 236 mg of 4,4'-dimethoxy-2,2'bithiophene in 5 mL of toluene. The mixture was heated and methanol was distilled off. The solution was then cooled to room temperature and washed with water and diethyl ether. The organic portion was separated and dried with magnesium sulfate. After evaporation, a brown solution was obtained which was purified by chromatography on silica gel using a mixture of CCl$_4$ and CHCl$_3$ (4:1) as the eluent. A greenish solid was obtained with a yield of 45%. M.P.: 171° C.

$^1$H NMR (CDCl$_3$, ppm): 6.85 (2H, d); 6.18 (2H,d); 4.27 (4H, t); 3.63 (4H, t)

$^{13}$C NMR (CDCl$_3$, ppm): 156.28; 136.27; 115.86; 97.79; 69.75; 28.75

Sodium 4,4'-di(2-sulfonate)ethoxy-2,2'-bithiophene

To a solution of 390 mg of Na$_2$SO$_3$ in 4.5 mL of water was added a solution of 73.3 mg of 4,4'-diethoxy-2,2'-bithiophene dissolved in 2 mL of acetone. Then 4 mL of water was added and the mixture was allowed to reflux for 48 hrs. The mixture was then washed with ether. The aqueous phase was separated and evaporated under reduced pressure. The crude product was dissolved in a mixture (1:1) of water and ethanol. The remaining inorganic salt precipitated and the suspension filtered. The aqueous phase was recovered and evaported. A yellowish solid was obtained with a yield of 50%. This product decomposes above 290° C. before melting.

$^1$H NMR (CDCl$_3$, ppm): 6.87 (2H, d); 6.40 (2H, d); 4.27 (2H, t); 3.25 (2H, t)

$^{13}$C NMR (CDCl$_3$, ppm): 156.28; 136.54; 116.47; 99.82; 66.16; 50.87

Example 4

Polymers 1.2 g of sodium 3-(2-sulfonate)ethoxy-4-methylthiophene and 3.0 g of dry FeCl$_3$ were mixed in 30 mL of chloroform and stirred for 24 hrs at room temperature. The mixture was poured into 500 mL of methanol where few drops of anhydrous hydrazine have been added. After this treatment, the polymer was put in 500 mL of a 1M NaOH methanolic solution. The precipitate was filtered and a dark blue powder was obtained (yield=50–60%).

Sodium poly(3-(2-sulfonate)ethoxythiophene) and sodium poly(4,4'-di(2-sulfonic cid)ethoxy-2,2'-bithiophene) have been prepared using a similar procedure. All resulting polymers showed a good solubility in water giving dark blue solutions.

SEC measurements revealed the polymers to have a number-average molecular weight of 6000 to 8000 with a polydispersity index of approximately 1.2.

FIGS. 1A to 3A show the UV-visible absorption spectra of
1A: Sodium poly(3-(2-sulfonate)ethoxythiophene),
2A: Sodium poly(3-(2-sulfonate)ethoxy-4-methylthiophene),
3A: Sodium poly(4,4'-di(2-sulfonate)ethoxy-2,2'-bithiophene).

These neutral polymers (conductivity lower than 10$^{-5}$ S/cm, measured on dry pressed pellets by the four probe method) were dissolved in water and passed through an ion-exchange resin column (H$^+$ type, Dowex HCR-W2), leading to the sulfonic acid form of these polymers.

This acid form of the substituted polythiophenes undergoes an oxidation reaction in air leading to a stable, conducting and nearly colorless state.

FIGS. 1B to 3B show the UV-visible absorption spectra of
1B: Poly(3-(2-sulfonic acid)ethoxythiophene),
2B: Poly(3-(2-sulfonic acid)ethoxy-4-methylthiophene),
3B: Poly(4,4'-di(2-sulfonic acid)ethoxy-2,2'-bithiophene).

Measurements of the electrical conductivity of the polythiophene derivatives yielded the following results:

| Sample | Conductivity [S/cm] |
|---|---|
| Poly(3-(2-sulfonic acid)ethoxythiophene): | 0.4 |
| Poly(3-(2-sulfonic acid)ethoxy-4-methylthiophene): | 5 |
| Poly(4,4'-di(2-sulfonic acid)ethoxy-2,2'-bithiophene): | 10 |

The doping and conductivity levels found for these polythiophenes are higher than those previously reported for poly(3-(ω-sulfonic acid)alkylthiophenes), which show conductivities in the range of $10^{-2}$ to $10^{-1}$ S/cm. They also have lower oxidation potentials of 0.0 to 0.6 V vs. SCE as compared to 0.8 to 1.0 V vs. SCE for the poly(3-(ω-sulfonic acid)alkylthiophenes). The polymers show an excellent stability in the acid (doped) state and no decrease of the electrical conductivity was observed as a function of time.

What is claimed is:

1. A thiophene corresponding to formula (I)

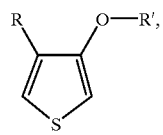
(I)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

2. A bithiophene corresponding to formula (IIa)

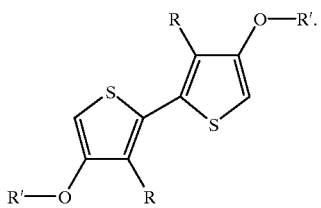
(IIa)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

3. A bithiophene corresponding to formula (IIb)

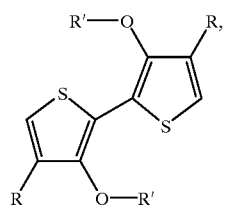
(IIb)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

4. A polymer comprising recurring units of formula (III)

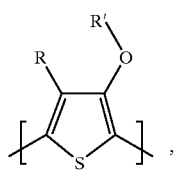
(III)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

5. A polymer comprising recurring units of formula (IVa)

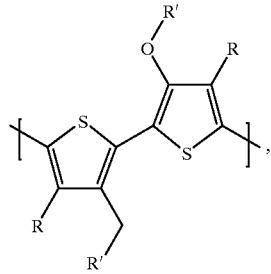
(IVa)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

6. A polymer comprising recurring units of formula (IVb)

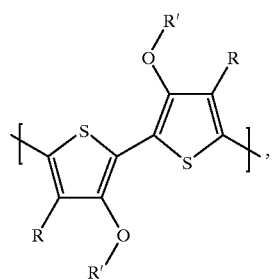
(IVb)

in which R is a hydrogen atom or a $C_1$–$C_4$ alkyl group and R' is —$(CH_2)_n$—$SO_3M$ with n=2 to 12 and M=H, Li, Na, K, Rb, Cs, $NH_4$.

7. A process for the preparation of the thiophene of claim 1, comprising the steps of
   a) reacting a 3-bromothiophene with $NaOCH_3$ in the presence of CuBr to form a 3-methoxythiophene,
   b) reacting the 3-methoxythiophene with an ω-haloalkanol in the presence of $NaHSO_4$ to form a 3-(ω-haloalkoxy)thiophene,
   c) reacting the 3-(ω-haloalkoxy)thiophene with $M_2SO_3$ (M=H, Li, Na, K, Rb, Cs, $NH_4$) to form the thiophene of claim 1.

8. A process for the preparation of the bithiophene of claim 2, comprising the steps of
   a) reacting a 4,4'dibromo-2,2'-bithiophene with $NaOCH_3$ in the presence of CuBr to form a 4,4'-dimethoxy-2,2'-bithiophene,
   b) reacting the 4,4'-dimethoxy-2,2'-bithiophene with an ω-haloalkanol in the presence of $NaHSO_4$ to form a 4,4'-di(ω-haloalkoxy)-2,2'-bithiophene,
   c) reacting the 4,4'-di(ω-haloalkoxy)-2,2'-bithiophene with $M_2SO_3$ (M=H, Li, Na, K, Rb, Cs, $NH_4$) to form the bithiophene of claim 2.

9. A process for the preparation of the bithiophene of claim 3, comprising the steps of
   a) reacting a 3,3'dibromo-2,2'-bithiophene with $NaOCH_3$ in the presence of CuBr to form a 3,3'-dimethoxy-2,2'-bithiophene, b) reacting the 3,3'-dimethoxy-2,2'-bithiophene with an ω-haloalkanol in the presence of $NaHSO_4$ to form a 3,3'-di(ω-haloalkoxy)-2,2'-bithiophene, c) reacting the 3,3'-di(ω-haloalkoxy)-2,2'-bithiophene with $M_2SO_3$ (M=H, Li, Na, K, Rb, Cs, $NH_4$) to form the bithiophene of claim 3.

10. A process for the preparation of the polymer of formula (III) by polymerizing the thiophenes of claim 1 in the presence of an oxidant.

11. A process for the preparation of the polymer of formula (IVa) by polymerizing the bithiophenes of claim 2 in the presence of an oxidant.

12. A process for the preparation of the polymer of formula (IVb) by polymerizing the bithiophenes of claim 3 in the presence of an oxidant.

13. An anti-static coating or EMI shielding comprising the polymer of claim 4.

14. An anti-static coating or EMI shielding comprising the polymer of claim 5.

15. An anti-static coating or EMI shielding comprising the polymer of claim 6.

* * * * *